United States Patent [19]

Umemura et al.

[11] Patent Number: 5,025,655
[45] Date of Patent: Jun. 25, 1991

[54] IMPACT TEST HAMMER

[75] Inventors: Kiyoshi Umemura, Kawasaki; Teruo Irie, Tokyo, both of Japan

[73] Assignee: Yamaichi Electric Mfg. Co., Ltd., Tokyo, Japan

[21] Appl. No.: 507,116

[22] Filed: Apr. 10, 1990

[30] Foreign Application Priority Data

Apr. 12, 1989 [JP] Japan .............................. 1-42800[U]

[51] Int. Cl.$^5$ ............................................. G01N 3/30
[52] U.S. Cl. ......................................... 73/11; 173/12
[58] Field of Search ..................... 173/1, 11, 12, 20; 73/11, 12, 572

[56] References Cited

U.S. PATENT DOCUMENTS

| | | | |
|---|---|---|---|
| 3,435,658 | 4/1969 | Arthur | 73/12 |
| 3,538,743 | 11/1970 | Glidden | 73/12 |
| 4,399,685 | 8/1983 | Atkey | 73/11 |
| 4,422,320 | 12/1983 | Moorby et al. | 73/12 |
| 4,615,209 | 10/1986 | Change, Jr. | 73/12 |
| 4,689,985 | 9/1987 | Glass, III | 73/12 |
| 4,799,375 | 1/1989 | Lally | 73/12 |
| 4,856,318 | 8/1989 | Hogan et al. | 73/12 |

Primary Examiner—Douglas D. Watts
Assistant Examiner—Scott A. Smith
Attorney, Agent, or Firm—Wenderoth, Lind & Ponack

[57] ABSTRACT

An impact test hammer includes a cylindrical handle having opposite first and second end portions and a hollow interior, a sensor portion fixed to the first end portion of the handle, and a grip portion fixed to the second end portion of the handle. An elastic striking portion is fixed to an outer periphery of the sensor storage portion, and an impact acceleration sensor is housed within the sensor storage portion for sensing a striking power of the elastic striking portion applied to a test object. A circuit is housed within the grip portion and operatively connected to the sensor by way of wiring extending through the hollow interior of the handle. Such a circuit includes a range switch, a scale conversion amplifier and a wind amplifier. A knob is provided on the outer periphery of the grip portion for operating the range switch to set a degree of amplification of the amplifier. The amplifier receives a signal from the sensor and amplifies the signal according to the amplification degree set by the range switch. The wind comparator outputs an indicator actuation signal when the output from the amplifier falls within a specified range which is determined based on the characteristics of the test object.

1 Claim, 2 Drawing Sheets

IMPACT TEST HAMMER

BACKGROUND OF THE INVENTION

1. Field of the Invention

This invention relates to an impact test hammer which is used for conducting impact tests of a test object such as, for example, an electronic circuit, an electronic part, a component part, etc., by applying a proper striking power to the test object, such proper striking power depending on the test object itself.

2. Brief Description of the Prior Art

When, for example, an electronic circuit, an electronic part or the like is impact tested, such a test object is usually set in a testing apparatus and the impact test is carried out by striking the test object within the testing apparatus using a hammer. The proper striking power is dependant upon each test object.

The conventional impact test hammer includes, as means for determining whether a proper striking power is being applied to the test object, a sensor device comprising a piezoelectric element housed in the hammer head portion. A battery acting as a power source and a buzzer actuated by an output signal of the sensor are all built in a grip portion, so that when the test object is struck with a striking power larger than the proper striking power, a voltage is output by the sensor to actuate the buzzer and thus inform a user who is carrying out the test that the test object is being struck with an excess striking power.

According to the conventional impact test hammer, when the test object is struck with a striking power which is larger than a proper striking power, a buzzer sound is generated. Accordingly, although there is a lower striking power limit, there is not an upper limit. Therefore, the buzzer sound is always generated when the test object is struck with a power which is larger than a proper striking power. As a result, it is difficult to carry out a reliable test in which the test object is always struck with a constant proper striking power.

Furthermore, the prior art impact test hammer is problematic in that is can be used only for one kind of test object and different test hammers must be used for each of a plurality of test objects having different proper striking powers.

SUMMARY OF THE INVENTION

It is therefore a principal object of the present invention to provide a single impact test hammer for correctly testing a plurality of test objects having different proper striking powers.

Another object of the present invention is to provide an impact test hammer for preventing a test object from being damaged by being struck with a striking power which is larger than necessary.

In order to achieve the above objects, there is provided an impact test hammer for impact testing a test object which includes a cylindrical handle having opposite first and second end portions and a hollow interior, a sensor storage portion fixed to the first end of the handle, a grip portion fixed to the second end portion of the handle, an elastic striking portion fixed to an outer periphery of the sensor storage portion, an impact acceleration sensor housed within the sensor storage portion for sensing a striking power of the elastic striking portion applied to the test object and for outputting a first signal corresponding to the striking power, a circuit housed within the grip portion and operatively connected to the sensor by wiring which passes through the hollow interior of the handle. The circuit includes a range switch, a scale conversion amplifier and a wind comparator. A knob is provided on an outer peripheral portion of the grip portion for operating the range switch to set a degree of amplification of the amplifier. The amplifier is for receiving and amplifying the first signal at the degree of amplification set by the range switch and for outputting a thus amplified second signal. The wind comparator is for receiving the second signal and for outputting a third signal when the second signal falls within a striking power range which is suitable for the test object. A battery is housed within the grip portion for actuating the circuit, and a switch is provided on an outer peripheral portion of the grip portion for turning on the battery. A light indicator is provided on an outer peripheral portion of the grip portion for illuminating in response to the third signal output by the wind comparator.

The impact test hammer of the present invention is used by switching the scale conversion amplifier in accordance with the test object. Only when the test object is struck with a striking power which is within a proper striking power range, does the wind comparator output a signal for actuating the indicator.

When the test object is struck with a striking power which is outside the upper and lower limits of the proper striking power range, the indicator is not actuated by the wind comparator, and the user thus recognizes that the striking power being currently applied to the test object is not proper. As a result, the fear is reduced that the test object will be struck and damaged by a larger striking power than is necessary. Also, when test objects having different proper striking powers are tested, the impact test may be properly performed by switching the scale conversion amplifiers as mentioned above. That is, a plurality of test objects can be properly tested using a single test hammer.

The above and other objects and features of the present invention will become apparent from the following description taken in conjunction with a preferred embodiment thereof shown in the accompanying drawings.

BRIEF DESCRIPTION OF THE DRAWINGS

The drawings show one embodiment of an impact measurement hammer according to the present invention, wherein.

DETAILED DESCRIPTION OF THE EMBODIMENT

An impact test hammer of the present invention will now be described with reference to the accompanying drawings in which one embodiment of the hammer construction is depicted.

Figure 1:
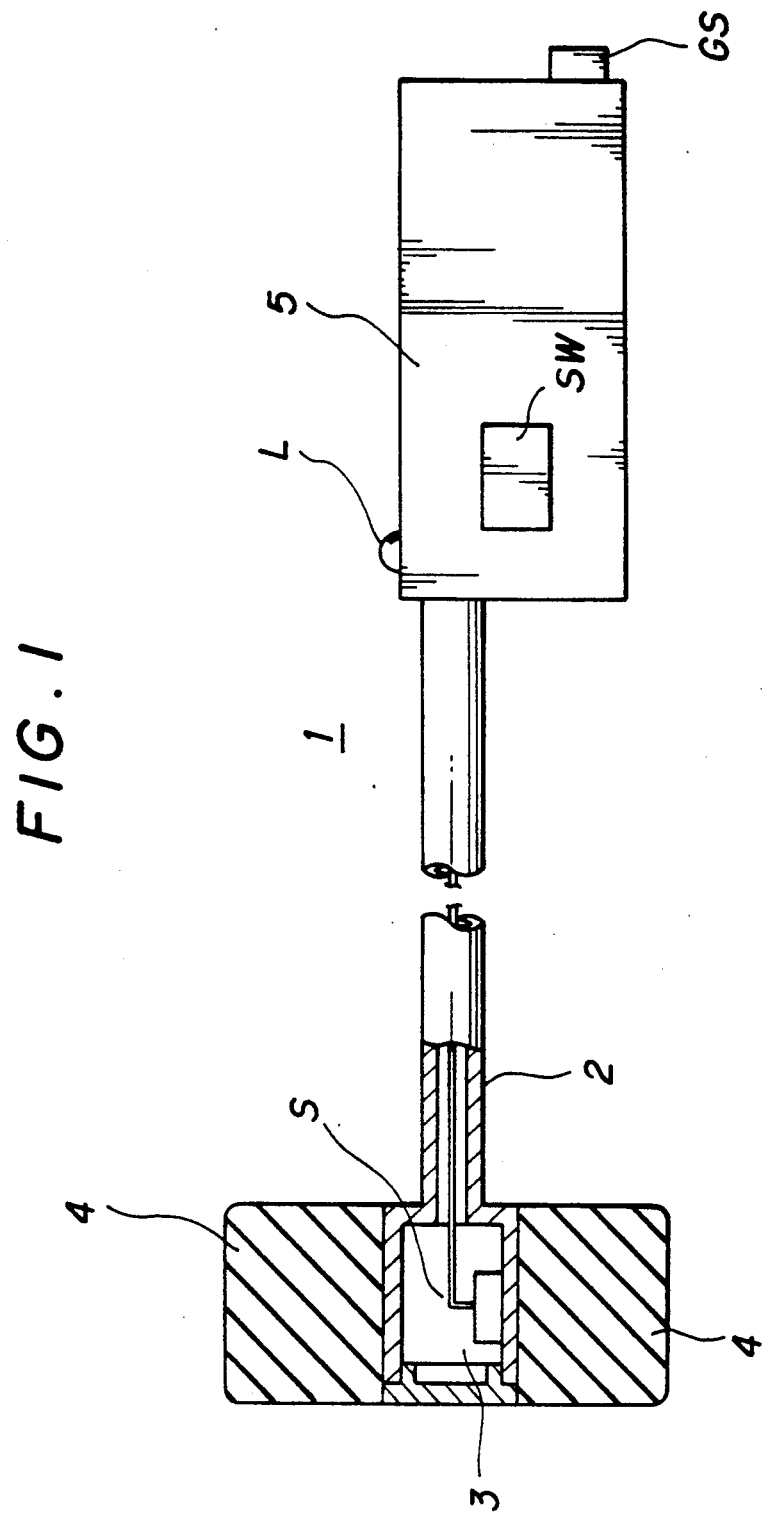
FIG. 1 is a partly cutaway side view of the entire hammer.

FIG. 1 shows an impact test hammer 1 of the present invention. The numeral 2 denotes a handle of the hammer 1. The handle 2 is cylindrically shaped and provided with a sensor storage portion 3 at a front end thereof. The sensor storage portion 3 houses a vibration sensor, for example an acceleration sensor S made up of a piezoelectric element, such as a ceramic piezoelectric element. The sensor storage portion 3 has associated therewith a striking portion 4 made of an elastic material, for example urethane rubber, which is fixed to an outer periphery of the sensor storage portion 3. The numeral 5 denotes a grip portion fixedly mounted on a rear end of the handle 2. A circuit configuration shown as in FIG. 2 is incorporated in the grip portion 5 and the sensor storage portion 3.

Figure 2:
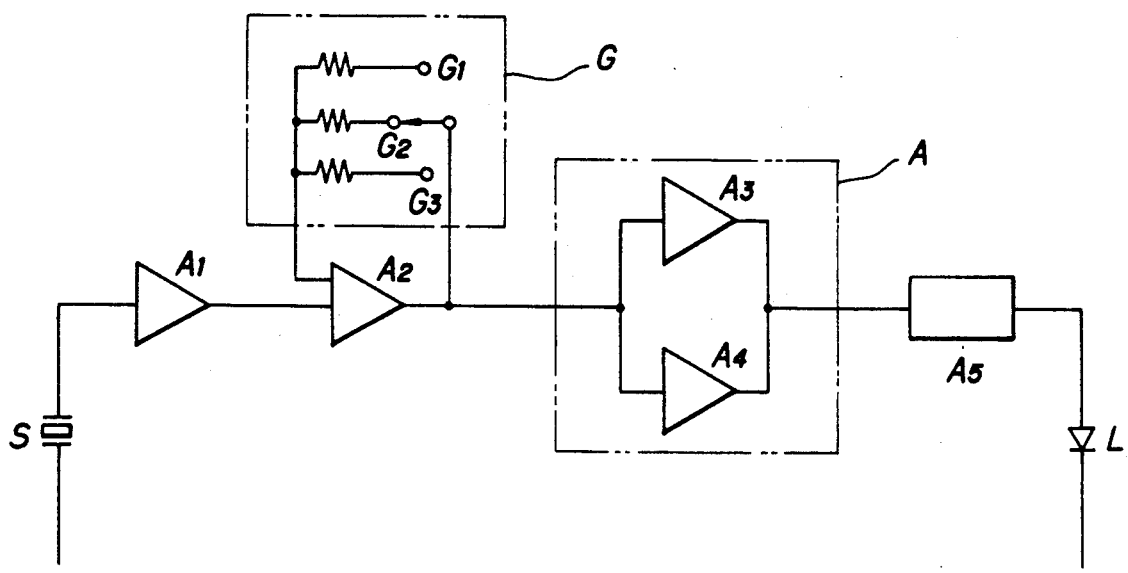
FIG. 2 is a circuit diagram of a circuit which is housed in the hammer of FIG. 1.

That is, in FIG. 2, S denotes an acceleration sensor housed in the sensor storage portion 3. The acceleration sensor S is adapted to generate an output signal (voltage signal) of a scale corresponding to the magnitude of a striking power. The reference character $A_1$ denotes a sensor signal amplifier connected to an output of the sensor S and adapted to amplify the output signal of the sensor S. The sensor signal amplifier Al is designed such that when the striking power magnitude of a proper striking power value $G_1$ of a certain test object is in the 60G to 80G range, a signal of 1.03V to 1.37V is output from the sensor signal amplifier $A_1$, and when the striking power magnitude of a proper striking power value $G_2$ of a certain test object is in the 120G to 160G range, a signal of 2.06V to 2.73V is output from the sensor signal amplifier $A_1$, and when a striking power magnitude of a properly striking power value $G_3$ of a certain test object is in the 180G to 240G range, a signal of 3.09V to 4.1V is output from the sensor signal amplifier $A_1$.

The reference character $A_2$ denotes a scale conversion amplifier connected to the output of the sensor signal amplifier $A_1$. The scale conversion amplifier $A_2$ includes a range switch G which can be switched, for example, between three stage switching contact points corresponding to proper striking power values $G_1$, $G_2$ and $G_3$ of the test object and is adapted to convert the amplification scale of a signal output from the amplifier $A_1$ and to thereby output a scale conversion signal.

In the case where an impact test for a test object having, for example, a proper striking power value of 60 to 80G (1.03 to 1.37V) is performed, the range switch G is switched to a switching contact point corresponding to the value $G_1$. As a result, a gain setting resistance is switched, the amplification degree of the amplifier $A_2$ is changed and a scale conversion corresponding to the amplification degree is carried out. Furthermore, a scale conversion signal of, for example, 2.06 to 2.74V, which is two times 1.03 to 1.37V, is output. Similarly, in the case where the range switch G is switched to switching contact points $G_2$ and $G_3$, the amplification degree is set corresponding to the respective gain setting resistance. Only signals in the range of such switched proper striking powers are picked up and an indicator L, such as a lamp device (for example, LED), is actuated.

Figure 3:
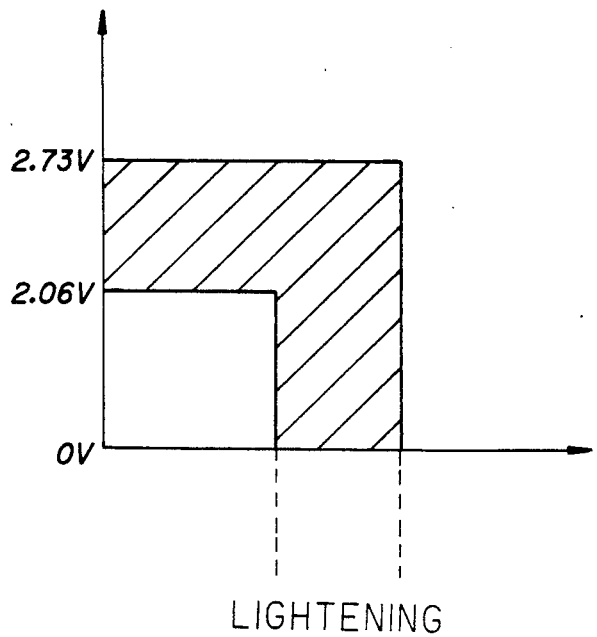
FIG. 3 is an explanatory view of the operation of the circuit of FIG. 2.

The reference character A denotes a wind comparator connected to the output side of the scale conversion amplifier $A_2$. The wind comparator A includes an upper limiter $A_3$ and a lower limiter $A_4$. Presuming, for example, that the upper limit of upper limiter $A_3$ is set to 2.73V and the lower limit of the lower limiter $A_4$ is set to 2.06V as shown in FIG. 3, the upper limiter $A_3$ outputs a signal of, for example, 5V, for actuating the indicator L when the signal is smaller than 2.73V and outputs a signal of 0V when the signal is larger than that, and the lower limiter $A_4$ outputs a signal of, for example, 5V, for actuating the indicator L when the signal is smaller than 2.06V and outputs a signal of 0V when the signal is larger than that. The wired OR of the upper and lower limiters $A_3$ and $A_4$ serve as an input signal of the indicator L. That is, when one of the limiters $A_3$ and $A_4$ outputs a signal of 5V an the other outputs a signal of 0V, and actuation signal of the indicator L can be obtained, and when both limiters $A_3$ and $A_4$ output 5V, an actuation signal of the indicator L can be obtained. That is, only when a signal within a range of the lower limit (2.06V) and the upper limit (2.73V) of both limiters $A_3$ and $A_4$ is input to the wind comparator A, the actuation signal for the indicator L is output.

Although the upper limit and lower limit are set within a range of 2.06V and 2.73V equal to the proper striking power value $G_2$ in the above embodiment, the present invention is, as a matter of course, not limited to this.

The reference character $A_5$ denotes a timer connected to the output side of the wind comparator A. The timer $A_5$ is adapted to set the activation period of the indicator L as shown in FIG. 3. It is noted that the indicator L may be a buzzer.

As to the construction of the circuit mentioned above, the entire circuit excluding the acceleration sensor S is housed in the grip portion 5 of the hammer I, together with a power source battery, and is connected with the acceleration sensor S disposed in the sensor storage portion 3 by wiring through the handle 2. Also, the amplifier $A_1$ may be disposed within the sensor storage portion 3.

An operation knob GS of the range switch G is disposed at a suitable place on the grip portion 5, for example at a rear end face of the grip portion 5. A power switch SW is disposed on a surface of the grip portion 5 so that the power switch SW is depressed by the palm of the hand when the grip portion 5 is gripped and the power source is thus turned on. The indicator L is disposed in a position where the indicator L is not hidden by the hand when the grip portion 5 is gripped.

In FIG. 2, the power source battery and a circuit for stabilizing the same are omitted.

The operation of the impact measurement hammer of the present invention will be described. In order to simplify the explanation thereof, there will be described a case where a test object having a proper striking power value of 120 to 160G is tested. First, the operation knob GS of the range switch G is switched to a switching contact point corresponding to the proper striking power value $G_2$.

When, for example, a testing object previously set in a testing device is struck with the hammer I, a signal (voltage) of a scale corresponding to the magnitude of the striking power is generated by the sensor S.

This signal is amplified into a predetermined scale by the sensor signal amplifier $A_1$. That is, when the test object is struck with a striking power within a range of 60G to 80G, a signal within a range of 1.03V to 1.37V is generated. On the other hand, when the test object is struck with a striking power within a range of 120G to 160G, a signal within a range of 2.06V to 2.73V is generated. Likewise, when the testing object is struck with a striking power within a range of 180G to 240G, a signal within a range of 3.09V to 4.11V is generated. That is, a signal having a different scale depending on the magnitude of the striking power is output from the sensor signal amplifier $A_1$. Such various scales of output signals are amplified by the scale conversion amplifier $A_2$ in accordance with the amplification degree set by the range switch G, that is, the signal is converted in its scale and then output.

Such a scale converted output signal is input in the wind comparator A of the next stage. In this wind comparator A, only when a voltage signal input thereto is within the range (2.06V to 2.73V) set by the lower limiter $A_4$ and the upper limiter $A_3$, is there output a signal for actuating the indicator.

By this output, the indicator, for example a lamp L, is activated for a period of time set by the timer $A_5$ as shown in FIG. 3.

Presuming, for example, that the amplification degree, which was set in the manner as mentioned above, is 1, when the test object is struck with a striking power of 60G to 80G, a signal of 1.03 to 1.37V is output as it is, and when the test object is struck with a striking power of 120G to 160G, a signal of 2.06V to 2.73V is output. Likewise, when the test object is struck with a striking power of 180 to 240G, a signal of 3.06 to 4.11V is output as it is. In the wind comparator A, only when a signal of 2.06 to 2.73V is input thereto, the indicator L is actuated. The user can recognize from the illumination of the indicator L, for example, that the test object is being struck with a proper striking power.

In the illustrated example, although the range switch of the scale conversion amplifier $A_2$ is of three stages and a signal hammer can be used for different test objects in such three states, the hammer of the present invention is not limited to the illustrated example. Instead, the number of the range switching stages can be desirably selected.

As described in the foregoing, according to an impact test hammer of the present invention, the scale conversion amplifier is switched depending on the characteristics of the different test objects, and only when the test objects are struck with proper striking powers, which are different depending on the test objects, the wind comparator outputs a signal for actuating the indicator. That is, in the case where objects having different proper striking powers are tested, such a plurality of test objects can be tested using a single hammer by simply switching the scale conversion amplifier as mentioned above.

When such test objects are struck with a striking power of a magnitude outside the lower and upper limits of proper striking power, the indicator is not to be actuated by the wind comparator. Accordingly, the user can recognize that the striking power currently being applying to the test object is not proper. Therefore, there can be avoided such an incidence where the test object is struck and damaged with a striking power stronger than necessary while not knowing that the test object is being struck with such an improper striking power.

What is claimed is:

1. An impact test hammer for impacting a test object, said impact test hammer comprising:
   a cylindrical handle having opposite first and second end portions and a hollow interior;
   a sensor storage portion fixed to said first end portion of said handle;
   a grip portion fixed to said second end portion of said handle;
   an elastic striking portion fixed to an outer periphery of said sensor storage portion;
   an impact acceleration sensor housed within said sensor storage portion for sensing a striking power of said elastic striking portion applied to the test object and for outputting a first signal corresponding to said striking power;
   a circuit housed within said grip portion and operatively connected to said sensor by wiring which passes through said hollow interior of said handle, said circuit comprising a range switch, a scale conversion amplifier and a wind comparator;
   a knob provided on an outer peripheral portion of said grip portion for operating said range switch to set a degree of amplification of said amplifier;
   said amplifier for receiving and amplifying said first signal at the degree of amplification set by said range switch and for outputting a thus amplified second signal;
   said wind comparator for receiving said second signal and for outputting a third signal when said second signal is indicative of a striking power that falls within a striking power range which is suitable for the test object;
   a battery housed within said grip portion for actuating said circuit;
   a switch provided on the outer peripheral portion of said grip portion for turning on said battery; and
   a light indicator provided on the outer peripheral portion of said grip portion for illuminating in response to said third signal being output by said wind comparator.

* * * * *